United States Patent [19]

Purrmann et al.

[11] Patent Number: 4,927,866

[45] Date of Patent: May 22, 1990

[54] SHAPABLE MATERIAL AND SHAPED ARTICLES OBTAINABLE THEREFROM

[75] Inventors: Robert Purrmann, Starnberg; Rainer Guggenberger, Hechendorf; Gunter Pieper, Seefeld, all of Fed. Rep. of Germany

[73] Assignee: ESPE Stiftung & Co. Produktions- und Vertriebs KG, Seefeld, Fed. Rep. of Germany

[21] Appl. No.: 316,946

[22] Filed: Feb. 28, 1989

[30] Foreign Application Priority Data

Feb. 29, 1988 [DE] Fed. Rep. of Germany ....... 3806448

[51] Int. Cl.$^5$ .............................................. A61K 6/08
[52] U.S. Cl. ...................................... 523/115; 524/2; 524/5; 523/116
[58] Field of Search .................... 523/115, 116; 525/2, 525/5; 521/97

[56] References Cited

U.S. PATENT DOCUMENTS

| | | |
|---|---|---|
| 4,296,209 | 10/1981 | Tomic .................................. 521/85 |
| 4,376,835 | 3/1983 | Schmitt et al. ...................... 523/116 |
| 4,758,612 | 7/1988 | Wilson et al. ....................... 523/116 |

FOREIGN PATENT DOCUMENTS

WO85/00291 1/1985 PCT Int'l Appl. .

*Primary Examiner*—Joseph L. Schofer
*Assistant Examiner*—Jeffrey T. Smith
*Attorney, Agent, or Firm*—Birch, Stewart, Kolasch & Birch

[57] ABSTRACT

A shapable material is disclosed which contains:
(a) an aluminum fluorosilicate glass;
(b) at least one polycarboxylic acid having an average molecular weight greater than 500;
(c) a carbonate and/or hydrogen carbonate in an amount of at least 0.1% by weight, based on (a);
(d) optionally a chelating agent; and
(e) optionally water.

Said material is especially suited as bone replacement material and can be shaped into porous articles.

22 Claims, No Drawings

SHAPABLE MATERIAL AND SHAPED ARTICLES OBTAINABLE THEREFROM

BACKGROUND OF THE INVENTION

The invention relates to a shapable material, having particular suitability as a bone replacement material, and to shaped articles obtainable therefrom.

In the course of surgical operations the surgeon frequently is faced with the problem of repairing natural bone defects or bone defects caused in the course of an operation. As bone replacement material, there are primarily used "bioinert" or "bioactive" materials known by such terms as "bioceramics", "bioglasses" and "bioglass ceramics". "Bioinert" in this context has been used to describe materials that do not trigger any tissue reaction and that do not release any alien substances. Implants having on their surface a layer of titanium oxide, which functions as a bioinert layer can be included in the bioinert group of materials. "Bioactive" in today's language usage is used to describe materials having the property of directly accreting with bone tissue. They include bioglasses and bioglass ceramics having on the surface distinct proportions of calcium phosphate ceramics, e.g., hydroxyl apatite ceramics and tricalcium-phosphate ceramics. As bone replacement material, various hydroxyl apatite ceramics and tricalciumphosphate ceramics are employed which are available on the market in granulated form and as prefabricated shaped parts. The preparation of the materials involves rather expensive sinter processes in which micro and macro porosities are obtained by applying heat and using certain additives.

Furthermore, for remedying bone defects, it has been known to use implantation materials of polyacrylates with filler particles on the basis of tricalcium phosphate (German Offen. 33 25 111) German Offen 33 25 111 also describes that it may be advantageous to add further physiologically tolerable resorptive substances besides tricalcium phosphate, wherein resorption produces porosity on the surface of the replacement material, thus facilitating the accretion of bone material.

German Offen. 27 52 297 similarly describes filled polymethyl methacrylate materials containing carbonates and phosphoric acid, besides a resorbable filler, e.g., $Na_2HPO_4$. By joint action of phosphoric acid and carbonate, a porous structure of material is formed when they are mixed (after foaming). Since the materials contain liquid monomers and phosphoric acid, they are not harmless under a toxicological aspect. Moreover, high temperatures may occur in the course of the hardening reaction whereby neighboring tissue may be destroyed. In view of this fact a "bioactive" effect is hardly possible.

In the areas of dentistry so-called "glassionomer cements" have been used. These are reaction products of an aluminum fluorosilicate glass powder and a water-soluble polycarboxylic acid and water. These materials are used primarily as tooth filling material, i.e., dental cement material; they are also used as bone cement, i.e. for anchoring dentures in the bone (e.g., German Offen. 29 29 121).

SUMMARY OF THE INVENTION

It is accordingly an object of the present invention to provide a shapable material which is easy to prepare, which does not contain toxicologically objectionable low molecular weight monomers, which material can be shaped with foaming and curing without the use of strong acids, and which foaming and curing results in shaped structures having a porous texture.

Furthermore, one of the objects of the present invention is to provide a shapable material containing:
(a) an aluminum fluorosilicate glass;
(b) at least one polycarboxylic acid having an average molecular weight greater than 500;
(c) a carbonate and/or hydrogen carbonate in an amount of at least 0.1% by weight, based on (a);
(d) optionally a chelating agent; and
(e) optionally water.

Shaped articles obtainable from the above said material by curing are also provided.

DETAILED DESCRIPTION OF THE INVENTION

The materials disclosed in the present invention are suited especially for use as bone replacement material.

By the addition of water the non-hydrous ingredients in the material of the invention cure with foaming, and at this stage it can be shaped.

The hydrous material of the invention can be stored in form of at least two spatially separated components, of which preferably at least one component is solid, and preferably pulverulent, and one further component which is liquid or pasty.

Some preferable mixtures of solid, preferably pulverulent components, and corresponding liquid components are the following:

| solid component (constituents) | liquid component (constituents) |
| --- | --- |
| (a) + (c) | $H_2O$ + (b), optionally (d) |
| (a) + (c) + (b) | $H_2O$, optionally (d) |
| (a) + (c) + (d) | $H_2O$ + (b) | wherein:
(a) = an aluminum fluorosilicate glass;
(b) = at least one polycarboxylic acid having a molecular weight greater than 500;
(c) = a carbonate and/or hydrogen carbonate in an amount of at least 10% by weight, based on (a); and
(d) = a chelating agent.

When solid and liquid components, such as the above, are put together for processing the material of the invention, a shaped article is formed by the reaction of the polycarboxylic acid with the aluminum fluorosilicate glass, and the simultaneous reaction of the polycarboxylic acid with the carbonate and/or hydrogen carbonate forms macropores in the structure.

In a preferred embodiment, the material disclosed in the present invention consists of a liquid component containing 40 to 90% by weight of water, 10 to 60% by weight of polycarboxylic acid, and optionally 0 to 20% by weight of chelating agent, and a solid component containing 80 to 99.9% by weight of aluminum fluorosilicate glass and 0.1 to 20% by weight of a carbonate and/or hydrogen carbonate.

A further preferred embodiment of the material disclosed in the present invention consists of a liquid component containing 80 to 100% by weight of water and 0 to 20% by weight of chelating agent, and of a solid component containing 50 to 95% by weight of aluminum fluorosilicate glass, 4.9 to 50% by weight of dry polycarboxylic acid, and 0.1 to 20% by weight of carbonate and/or hydrogen carbonate.

The materials disclosed to the present invention may additionally contain, for example, preservatives such as benzoic acid, and thixotropy adjuvants, fillers, pigments, etc.

The shaped articles that can be produced with the material according to the invention can be slightly abraded on the surface before being put to use so that the pores therein become exposed.

With the materials encompassed by the invention, the advantages of biologically compatible and advantageous materials, such as hydroxyl apatite ceramics, may be combined, with the ease of applicabilty of filled polyacrylates, without having to cope with past drawbacks, such as the addition of resorbable substances, the use of strong acids, the use of toxicologically objectionable monomers, and difficulties encountered in the shaping of hard ceramic and glass materials.

Pasty compositions can be prepared with the materials disclosed in the present invention for use as a substitute bone material which can be formed into a desired shape by a surgeon during an operation in a simple manner without the use of cutting tools. Additionally, pasty compositions can be filled directly into the bone defects, and allowed to cure in situ. In this way, well tolerated bone replacement parts may be obtained and which, owing to their porosity, can be infiltrated and accreted by bone material in a patient's body. It is noted, the curing reaction of said materials does not harm the surrounding bone material by any of the effects of strong acid or high temperature, as occurred in certain previous methods.

It is an additional advantage of the present invention that the macroporosity can be influenced by the particle size and quantity of the carbonates and/or hydrogen carbonates employed, and by the selection of the solubility of the carbonates and polycarboxylic acid employed. In an ideal way the invention permits the production of bone replacing parts which resemble the surrounding bone material, especially the spongiosa, with respect to porosity.

It is a still further advantage of the materials provided in the present invention that the individual components can be applied in predosed form in a distribution means (e.g. capsules) as described, for example, in German Offen. 34 07 648. In a capsule distribution means, the powdered component is usually in the interior of the capsule, while the liquid component is contained in a pad at the capsule wall. Prior to the application, the contents of the pad are pressed —by means of a special activator —through a hole in the capsule wall into the capsule interior. By shaking, the contents are homogeneously blended. The material can be introduced from the capsule directly into the bone cavity. With this mode of application it is advantageous to store glass and carbonate and/or hydrogen carbonate in powder form in the capsule interior and to hold the aqueous polycarboxylic acid solution, and optionally the chelating agent, as liquid component in the pad.

The component (a) of the material disclosed in the present invention may consist of the calcium aluminum fluorosilicate glasses described in German Offen. 20 61 513 and in European patent publication 0 023 013 and the strontium aluminum fluorosilicate glasses described in European patent publication 0 241 277. The aluminum fluorosilicate glass powders useful in the invention consist (in addition to oxygen) preferably of:

| Component | Calculated as | % by Weight |
|---|---|---|
| Si | $SiO_2$ | 20–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 |

It should be noted that at least 1% by weight of CaO and/or SrO must be contained, and altogether 0 to 20% by weight, calculated as oxides, of B, Bi, Zn, Mg, Sn, Ti, Zr, La or other trivalent lanthanides, K, W, Ge and further additives that do not impair the properties and are physiologically acceptable. By the addition of 10 to 20% by weight of $La_2O_3$ the glasses can be rendered visible on the X-ray screen.

Preferably the powder particles consist of:

| Si as $SiO_2$ | 25 to 50% by weight |
|---|---|
| Al as $Al_2O_3$ | 10 to 40% by weight |
| Ca as CaO | 0 to 35% by weight |
| Sr as SrO | 0 to 35% by weight |
| F | 5 to 30% by weight |
| Na as $Na_2O$ | 0 to 8% by weight |
| P as $P_2O_5$ | 1 to 10% by weight | wherein at least 10% by weight of Ca (calculated as CaO) and/or Sr (calculated as SrO) are compulsory and 0 to 10% by weight of $B_2O_3$, $Bi_2O_3$, ZnO, MgO, $SnO_2$, $TiO_2$, $ZrO_2$, $La_2O_3$ or other oxides of trivalent lanthanides, $K_2O$, $WO_3$, $GeO_2$, and further additives that do not impair the properties and are physiologically unobjectionable.

Specially preferred are powders which contain:

| Si as $SiO_2$ | 25 to 45% by weight |
|---|---|
| Al as $Al_2O_3$ | 20 to 40% by weight |
| Ca as CaO | 10 to 30% by weight |
| F | 10 to 30% by weight |
| Na as $Na_2O$ | 1 to 8% by weight |
| P as $P_2O_5$ | 1 to 10% by weight |

The glass powders used according to the invention may have a minimum average particle size of 1 μm, but preferably at least 3 μm. The average particle size may be 1 to 20 μm, but is preferably 3 to 15 μm, and especially preferred is a particle size of 3 to 10 μm. The glass powders may have a maximum particle size of 150 μm, but preferably 100 μm, and especially preferred is 60 μm.

The thus obtained powders are then subjected, if desired, to a surface treatment as described in European Patent 0 023 013. To this end the glass powders are surface treated with acid, preferably at room temperature. For the treatment substances containing acidic groups are employed, e.g. hydrochloric acid, sulfuric acid, nitric acid, acetic acid, propionic acid, or perchloric acid which form soluble calcium salts or strontium salts, respectively.

The acids are used at a concentration of 0.01 to 10% by weight, preferably of 0.05 to 3% by weight. After the respective reaction period the powders are separated from the solution and thoroughly rinsed so that substantially no soluble calcium or strontium salts are left on the surface of the powder particles.

The polycarboxylic acids employed as component (b) in the material disclosed in the present invention, can be selected from polycarboxylic acids known in the preparation of glassionomer cement powder, e.g., polymaleic acid, polyacrylic acid, polyitaconic acid, and mixtures thereof or copolymers, especially the acrylic acid/itaconic acid copolymers and/or maleic acid/acrylic acid copolymers known from European Patent 0 024 056. The average molecular weight of the polycarboxylic acids to be used according to the invention is higher than 500. An average molecular weight of 1000 to 20,000 is advantageous, and 3000 to 10,000 are preferred molecular weights. The polycarboxylic acid is employed preferably at concentrations of 5 to 50% by weight, based on the component (a).

In order to attain high storage stabilities of the bone replacement materials prior to their use it is recommended to add preservatives, e.g. benzoic acid, especially to the dry polycarboxylic acid.

As component (d) the composition may contain a chelating agent as described in German Offen. 23 19 715. Preferably tartaric acid is used as chelating agent.

As foaming agent (c) the mixture may contain all carbonates and/or hydrogen carbonates; preferably they are at least partially soluble in the aqueous polycarboxylic acid solution which optionally contains the chelating agent. Physiologically tolerable carbonates are preferably employed, such as the carbonates and/or hydrogen carbonates of alkali and/or alkaline earth metals. The carbonates and hydrogen carbonates of magnesium, calcium and strontium are especially preferred.

The carbonates and/or hydrogen carbonates to be used as foaming component (c) are preferably employed at concentrations of 0.1 to 20% by weight, based on the component (a); preferably they are used at 0.5 to 5% by weight, especially preferred at 1 to 3% by weight concentrations.

The weight ratio of component (b) to component (c) is preferably at least 3:1; a weight ratio of at least 10:1 is especially preferred.

The carbonates and/or hydrogen carbonates preferably have an average particle size of 0.1 to 200 μm, preferred is a particle size f 1 to 100 μm, and especially preferred a size from 5 to 50 μm.

The solubility of the carbonates and/or hydrogen carbonates can be controlled by the selection of the cation(s). It ought to be so dimensioned that the foaming process lasts until incipient curing. If rapid curing is desired, it is advisable to select readily soluble alkali metal carbonates and/or hydrogen carbonates, for slow curing the more sparingly soluble carbonates and/or hydrogen carbonates should be selected.

EXAMPLES

The aluminum fluorosilicate compositions used in the examples are compiled in Table 1.

TABLE 1

| | % by Weight | |
|---|---|---|
| | A | B |
| Si as $SiO_2$ | 25.5 | 27.6 |
| Al as $Al_2O_3$ | 20.5 | 26.0 |
| Ca as CaO | 14 | 28.8 |
| F | 15 | 17.0 |
| Na as $Na_2O$ | 2 | 2.1 |
| P as $P_2O_5$ | 4 | 8.3 |
| La as $La_2O_3$ | 20 | 0 |

EXAMPLE 1

Radiopaque curable pasty bone replacement material 100 parts by weight of a calcium aluminum fluorosilicate glass powder of the composition A in Table 1 (average particle size 6 μm) are blended with 1 part by weight of calcium carbonate (Messrs. Merck, average particle size 40 μm) and 20.3 parts by weight of a copolymer (1:1) of acrylic acid and maleic acid average molecular weight 7000 to form a homogeneous powder. (The dry copolymer is stabilized with 0.9% by weight of benzoic acid, based on the copolymer).

3.4 parts by weight of the thus obtained powder blend A are homogeneously mixed with 1 part by weight of distilled $H_2O$ (mixed for half a minute). During the processing period of 5 minutes (starting with the commencement of mixing) the material foams and, after 15 minutes, has turned into a solid foamed shaped article.

In order to determine the compression strength, 5 sample pieces (cylinders of 4 mm diameter and 7 mm height) are tested in a Zwick Universal Tester. The compression strength is 2.5 MPa, on the average.

The shaped pieces have pore sizes from 0.1 to 1.5 mm; the pores form an interconnected network.

The solubility is determined according to ISO/DIS specification 7489 for glassionomer cement and is 0.18%.

In order to determine the bioactivity, test pieces measuring 15×5×5 mm (2 pieces) and 15×10×2 mm (2 pieces) were implanted into the right fibula of a pavian. After 2 weeks, radiograms of the implanted pieces exhibited excessive bone growing activity, and after 4 more weeks they showed complete embedment of the test piece in newly formed bone material. Owing to the low solubility the material is not resorbed; the interpenetrating pores are completely filled with newly grown bone material.

EXAMPLE 2

Radiolucent Curable Pasty Bone Replacement Material 100 parts by weight of calcium aluminum fluorosilicate glass of the composition B in Table 1 are blended with 1 part by weight of calcium carbonate (Messrs. Merck, 40 μm) to form a homogeneous powder. 2 parts by weight of said powder are mixed with a solution consisting of 35% of copolymer of Example 1 and 65% $H_2O$ dist. to form a homogeneous paste. The material has a processing period of 4 minutes and 30 seconds (commencing with the beginning of mixing) and has turned completely hard after 12 minutes and 30 seconds. During this time the material foams to form a porous shaped body with pore sizes ranging between 0.1 and 1.5 mm; the compression strength of the material is 2.6 MPa, and the solubility is 0.19%, according to ISO/-DIS specification 7489.

Test pieces of the material measuring 15×20×5 mm (2 pieces) were implanted into the left tibia of a pavian. On the radiograms the implanted piece is poorly visible against the bone material. After 2 weeks overshooting bone formation is observed on the margin of the implanted piece, and after 4 more weeks the site can no longer be distinguished from the surrounding bone material since the implanted piece is completely intergrown with newly formed bone material.

EXAMPLE 3

Bone Replacement Material Prepared for Blending in a Capsule 700 mg of calcium aluminum fluorosilicate glass powder of the composition B in Table 1 and 7 mg of calcium carbonate (Merck, average particle size 2.3 μm) are weighed into the capsule interior of a commercial glassionomer capsule used in dentistry (KETACFIL, Messrs. ESPE). To the external capsule wall a pad containing 350 mg of a 35% by weight copolymer solution in $H_2O$ dist. is attached and thereafter activated and shaken like the corresponding glassionomer filling materials (Silamat, Messrs. Ivoclar, 4300 vibrations per minute, shaking period 10 minutes). The material has a processing period of 2 minutes, 10 seconds and cures after 5 minutes. The compression strength is 7 MPa and the solubility according to ISO/DIS specification 7489 is 0.18%. The pores show a size of 0.1 to 1.2 mm and form a communicating network.

We claim:

1. A shapable material comprising:
   (a) an aluminum fluorosilicate glass;
   (b) at least one polycarboxylic acid having an average molecular weight greater than 500;
   (c) a carbonate and/or hydrogen carbonate in an amount of at least 0.1% by weight, based on (a);
   (d) optionally a chelating agent; and
   (e) optionally water.

2. Shapable material according to claim 1, characterized in that it is in the form of at least two spatially separate components.

3. Shapable material according to claim 2, characterized in that at least one component is present in solid, preferably pulverulent form, and at least one other component is present in liquid or pasty form.

4. Shapable material according to claim 3, characterized in that the solid component contains the ingredients (a) and (b), and the liquid component contains the ingredients (c) and (e), and optionally the ingredient (d).

5. Shapable material according to claim 3, characterized in that the solid component contains the ingredients (a), (b) and (c), and the liquid component contains the ingredients (e) and optionally (d).

6. A shaped article obtainable by curing a shapable material according to one of claims 1 to 5.

7. A shapable bone replacement composition comprising:
   (a) an aluminum fluorosilicate glass;
   (b) at least one polycarboxylic acid having an average molecular weight greater than 500;
   (c) a carbonate and/or hydrogen carbonate in an amount of at least 0.1% by weight, based on (a);
   (d) optionally a chelating agent; and
   (e) optionally water.

8. The shapable composition of claim 7 in the form of at least two spatially separate components.

9. The shapable composition of claim 8 in the form of at least one solid component, and at least one liquid or pasty component.

10. The shapable composition of claim 9 wherein said solid component comprises ingredients (a) and (b), and said liquid or pasty component comprises ingredients (c), (e) and optionally (d).

11. The shapable composition of claim 9 wherein said solid component comprises ingredients (a), (b) and (c), and said liquid or pasty component comprises ingredients (e) and optionally (d).

12. The composition of claim 7, optionally comprising a preservative.

13. A method of preparing a bone replacement part, which method comprises the steps of:
   (I) mixing ingredients to form a pasty composition comprising:
      (a) an aluminum fluorosilicate glass;
      (b) at least one polycarboxylic acid having an average molecular weight greater than 500;
      (c) a carbonate and/or hydrogen carbonate in an amount of at least 0.1% by weight, based on (a);
      (d) optionally a chelating agent; and
      (e) optionally water;
   (II) shaping said composition as desired; and
   (III) allowing said composition to cure.

14. The method of claim 13 wherein prior to step (II), said composition is applied to the site of a bone defect.

15. The method of claim 13 wherein the exposed surfaces of said composition are abraded after curing.

16. The method of claim 14 wherein the exposed surfaces of said composition are abraded after curing.

17. A bone replacement part made by the method of claim 13.

18. A bone replacement part made by the method of claim 14.

19. A bone replacement part made by the method of claim 15.

20. A bone replacement part made by the method of claim 16.

21. A method of remedying bone defects, which method comprises the steps of:
   (I) mixing ingredients to form a pasty composition comprising:
      (a) an aluminum fluorosilicate glass;
      (b) at least one polycarboxylic acid having an average molecular weight greater than 500;
      (c) a carbonate and/or hydrogen carbonate in an amount of at least 0.1% by weight, based on (a);
      (d) optionally a chelating agent; and
      (e) optionally water;
   (II) applying said pasty composition to the site of a bone defect;
   (III) shaping said composition as desired; and
   (IV) allowing said composition to cure in place.

22. The method of claim 21, wherein the exposed surfaces of said composition are abraded after curing.

* * * * *

REEXAMINATION CERTIFICATE (1639th)
United States Patent [19]

Purrmann et al.

[11] B1 4,927,866

[45] Certificate Issued Feb. 4, 1992

[54] SHAPABLE MATERIAL AND SHAPED ARTICLES OBTAINABLE THEREFROM

[75] Inventors: Robert Purrmann, Starnberg; Rainer Guggenberger, Hechendorf; Gunter Pieper, Seefeld, all of Fed. Rep. of Germany

[73] Assignee: ESPE Stiftung & Co. Produktions- und Vertriebs KG

Reexamination Request:
No. 90/002,192, Oct. 31, 1990

Reexamination Certificate for:
Patent No.: 4,927,866
Issued: May 22, 1990
Appl. No.: 316,946
Filed: Feb. 28, 1989

[30] Foreign Application Priority Data

Feb. 29, 1988 [DE] Fed. Rep. of Germany ....... 3806448

[51] Int. Cl.⁵ ................................................ A61K 6/08
[52] U.S. Cl. ................................... 523/115; 523/116; 524/2; 524/5
[58] Field of Search .................... 523/115, 116

[56] References Cited

U.S. PATENT DOCUMENTS 4,209,434  6/1980  Wilson et al. .................. 526/303
4,705,810  11/1987  Millet et al. .................... 521/92

FOREIGN PATENT DOCUMENTS 1548419  7/1979  United Kingdom .

*Primary Examiner*—Edward J. Smith

[57] ABSTRACT

A shapable material is disclosed which contains:
(a) an aluminum fluorosilicate glass;
(b) at least one polycarboxylic acid having an average molecular weight greater than 500;
(c) a carbonate and/or hydrogen carbonate in an amount of at least 0.1% by weight, based on (a);
(d) optionally a chelating agent; and
(e) optionally water.

Said material is especially suited as bone replacement material and can be shaped into porous articles.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 21 and 22 is confirmed.

Claims 1-13, 15, 17 and 19 are cancelled.

Claim 14 is determined to be patentable as amended.

Claims 16, 18 and 20, dependent on an amended claim, are determined to be patentable.

New claims 23 and 24 are added and determined to be patentable.

14. [The] *A* method of [claim 13 wherein prior to step (II), said composition is applied to the site of a bone defect] *preparing a bone replacement part, which method comprises the steps of:*
   *(I) mixing ingredients to form a pasty composition comprising:*
   *(a) an aluminum fluorosilicate glass,*
   *(b) at least one polycarboxylic acid having an average molecular weight of greater than 500,*
   (c) a carbonate and/or hydrogen carbonate in an amount of at least 0.1% by weight, based on (a),
   (d) optionally a chelating agent, and
   (e) optionally water;
   (II) applying the composition to the site of a bone defect;
   (III) shaping the composition as desired; and
   (IV) allowing the composition to cure.

23. *A method of preparing a bone replacement part, having an interpenetrating open pore system therein, which method comprises the steps of:*
   *(I) homogeneously mixing the following ingredients to form a pasty composition comprising:*
   *(a) an aluminum fluorosilicate glass;*
   *(b) at least one polycarboxylic acid having an average molecular weight greater than 500;*
   *(c) a carbonate and/or hydrogen carbonate having a particle size of 0.1 to 200 μm, present in an amount of at least 0.1% by weight, based on (a);*
   *(d) optionally a chelating agent; and*
   *(e) optionally water;*
   *(II) shaping said composition as desired; and*
   *(III) allowing said composition to cure.*

24. *A method of remedying bone defects, which method comprises the steps of:*
   *(I) homogeneously mixing the following ingredients to form a pasty composition comprising:*
   *(a) an aluminum fluorosilicate glass;*
   *(b) at least one polycarboxylic acid having an average molecular weight greater than 500;*
   *(c) a carbonate and/or hydrogen carbonate having a particle size of 0.1 to 200 μm, present in an amount of at least 0.1% by weight, based on (a);*
   *(d) optionally a chelating agent; and*
   *(e) optionally water;*
   *(II) applying said pasty composition to the site of a bone defect;*
   *(III) shaping said composition as desired; and*
   *(IV) allowing said composition to cure in place.*

* * * * *